United States Patent [19]

Welch

[11] 4,247,770
[45] Jan. 27, 1981

[54] AERIAL MINERAL SURVEY METHOD AND APPARATUS USING PULSED LASER BEAM TO VAPORIZE SURFACE MATERIAL

[76] Inventor: Albert B. Welch, 3920 Centenary Dr., Dallas, Tex. 75225

[21] Appl. No.: 940,290

[22] Filed: Sep. 7, 1978

[51] Int. Cl.³ .................... G01V 5/00; G01J 1/58; G01N 21/00; G01J 3/44
[52] U.S. Cl. .................... 250/253; 250/459; 356/73; 356/301; 356/318
[58] Field of Search .............. 356/301, 318, 73; 250/253, 255, 458, 459, 461 R

[56] References Cited

U.S. PATENT DOCUMENTS

| | | | |
|---|---|---|---|
| 3,463,591 | 8/1969 | Franken et al. | 356/318 |
| 3,625,613 | 12/1971 | Abell | 356/301 |
| 3,899,213 | 8/1975 | Fantasia et al. | 250/461 |
| 4,071,298 | 1/1978 | Falconer | 356/318 |

FOREIGN PATENT DOCUMENTS 2517631 7/1976 Fed. Rep. of Germany ........... 250/253

OTHER PUBLICATIONS

Karyakin, et al., "Possibility of Using Lasers for the Atomic Absorption Analysis of Geochemical Objects", VDC 621.375.8, translation of Zhurnal Prikladnoi Spektrokupii, vol. 18 (4), pp. 610-613, 4-73, Plenum Pub. Corp., N.Y.

Hirschfeld et al., "New Fields for Laser Raman Spectroscopy", Proc. Electro-Optical Systems Design Conf., N.Y. City, 9-16-79, pp. 418-427.

Margoshes et al., "Emission Spectrometry", Anal. Chem., vol. 40 (5), 4-68, pp. 223-245.

Primary Examiner—Alfred E. Smith
Assistant Examiner—Carolyn E. Fields
Attorney, Agent, or Firm—Richards, Harris & Medlock

[57] ABSTRACT

A high-energy laser (22) carried in an aircraft (10) directs a laser beam (16) downward to a point (18) on the earth's surface beneath the aircraft (10). The intensity of the laser beam (16) is such that the material at the point (18) of contact is vaporized and thereby caused to emit atomic emission spectra characteristic of the material. A spectrometer (28) carried in the aircraft (10) collects the resulting spectra which is analyzed to determine the type and quantity of chemical elements present in the vaporzied sample. The laser beam (16) is directed at the point (18) on the surface with sufficient energy and for a period of time so as to penetrate the surface layer and vaporize the underlying material more representative of the overall mineral composition present in the region of the sample. A second laser beam from laser (29) is directed to the point (18) of contact to generate radiation for Raman and fluorescence spectrometry.

16 Claims, 3 Drawing Figures

AERIAL MINERAL SURVEY METHOD AND APPARATUS USING PULSED LASER BEAM TO VAPORIZE SURFACE MATERIAL

TECHNICAL FIELD

The present invention pertains to airborne mineral surveying and more particularly to methods and apparatus for remotely vaporizing and spectrally analyzing a mineral sample.

BACKGROUND ART

Various types of passive remote sensors have been employed in attempts to deduce the composition of earth materials from an airborne platform. These includes gamma ray spectrometry which yields direct measurement of near-surface abundance of certain elements, but is limited in practice to only a few rare radioactive isotopes. Fluorescence spectrometry, applicable for several minerals, commonly yields data that are representative of surface contamination rather than the underlying mineral. Furthermore, the fluorescence spectra of different minerals tends to be ambiguous and are not indicative of the abundance of the elements or compounds being sought.

Therefore there exists a need for apparatus to rapidly analyze a great number of mineral samples for quantity and makeup by analysis means transported by a platform located a distance from the mineral samples.

DISCLOSURE OF THE INVENTION

An aircraft is equipped with a high-energy laser and a spectrometer. Both the laser beam generated by the laser and the spectrometer are aimed at a common point on the earth's surface along the aircraft track. As the aircraft traverses the survey area the laser is energized at selected intervals to vaporize material at a small spot on the surface below. The vaporized material produces atomic emission radiation which is characteristic of that material, this radiation is collected by the spectrometer and analyzed to determine the type and quantity of chemical elements present in the sample. The aiming of the laser beam and spectrometer is accomplished by a stabilized platform in the aircraft. Multiple samples are taken at each spot on the earth's surface so as to penetrate the outer layers and collect samples more representative of the bulk of material in the sample region.

BRIEF DESCRIPTION OF DRAWINGS

For a more complete understanding of the present invention and the advantages thereof, reference is now made to the following description taken in conjunction with the accompanying drawings in which.

DETAILED DESCRIPTION

Figure 1:
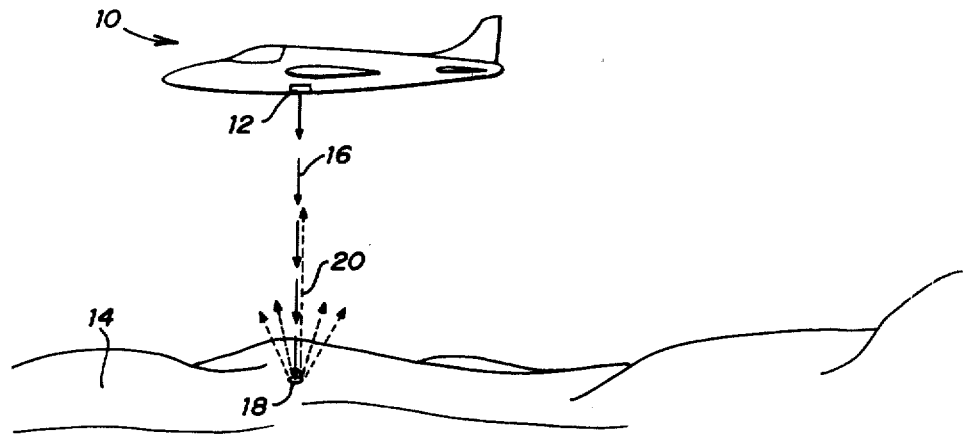
FIG. 1 is an elevation view of an aircraft for collecting mineral samples according to the present invention.

Referring to FIG. 1, there is shown an aircraft 10 carrying a mineral survey package 12 over a survey area 14. The package generates a laser beam 16 which is directed downward from the aircraft and strikes the survey area 14 at a sample point 18. The minerals at the sample point are vaporized and the resulting material produces radiation 20 which is projected outward over a wide range from the sample point 18. A portion of the radiation 20 is returned to the survey package 12 where it is analyzed to determine the makeup of the mineral structure at the sample point 18.

Figure 2:
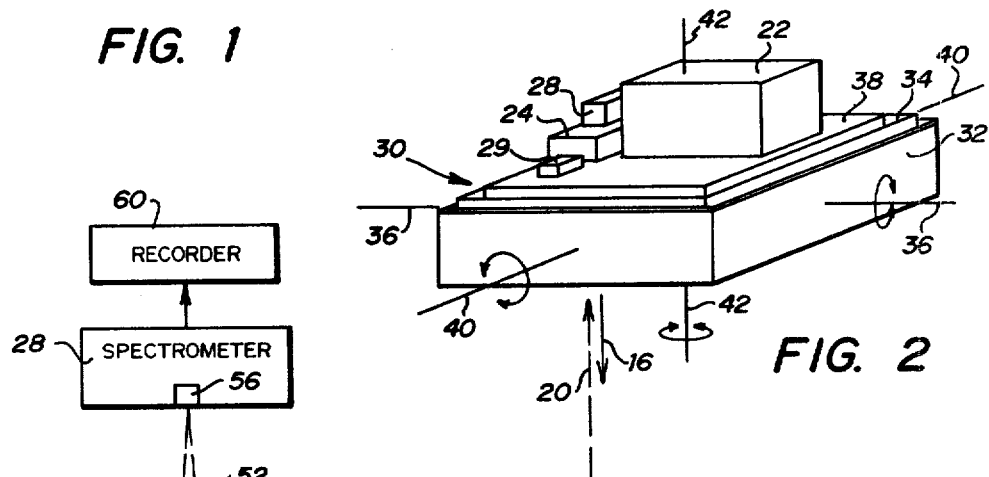
FIG. 2 is a perspective illustration of a laser beam generator and spectral analyzer mounted on a stabilized platform.

The survey package 12 is illustrated in further detail in FIG. 2. A high-energy laser 22 generates a laser beam which is directed to an optical system 24 that directs the laser beam 16 downward toward the earth. The resulting radiation 20 is returned to the survey package 12 where it is collected by the optical system 24 and transferred to a spectrometer 28 for mineral analysis. A relatively low power laser 29 generates a laser beam which is also directed downward to the sample point on the earth's surface.

The laser 22, optical system 24 and spectrometer 28 are mounted on a stabilized platform 30 for directing the laser beam 16 toward the sample point 18 on the earth. The platform 30 is connected to the aircraft fuselage by a fixed frame 32. Within the fixed frame 32 a roll gimbal 34 provides stabilization about a roll axis 36 and a pitch gimbal 38 provides stabilization about a pitch axis 40. The roll and pitch gimbals 34 and 38 are driven so as to direct the laser beam 16 to the selected point below the aircraft.

The stabilized platform 30 is inertially stabilized about two axes, roll and pitch. It is located so that the laser beam and spectrometer field-of-view are directed downward in approximate coincidence with the yaw axis 42 of the aircraft to minimize the effect of yawing motion on the pointing of the beam. An inertial reference sensor on the platform 30 senses any residual 3-axis motion of the platform with respect to inertial space and provides torquing commands to pitch and roll gimbals. Rate bias commands, derived from ground speed and altitude-above-ground, are provided to compensate for translation of the aircraft during activation of the laser and spectrometer.

The altitude information is also applied to adjust the focus of the laser beam expander and spectrometer optics, described below, to maintain the ground surface within the depth of focus of the optics. Other well known optical stabilization methods, such as the inertia-referenced coelostat, may be substituted for the stabilized platform 30.

Figure 3:
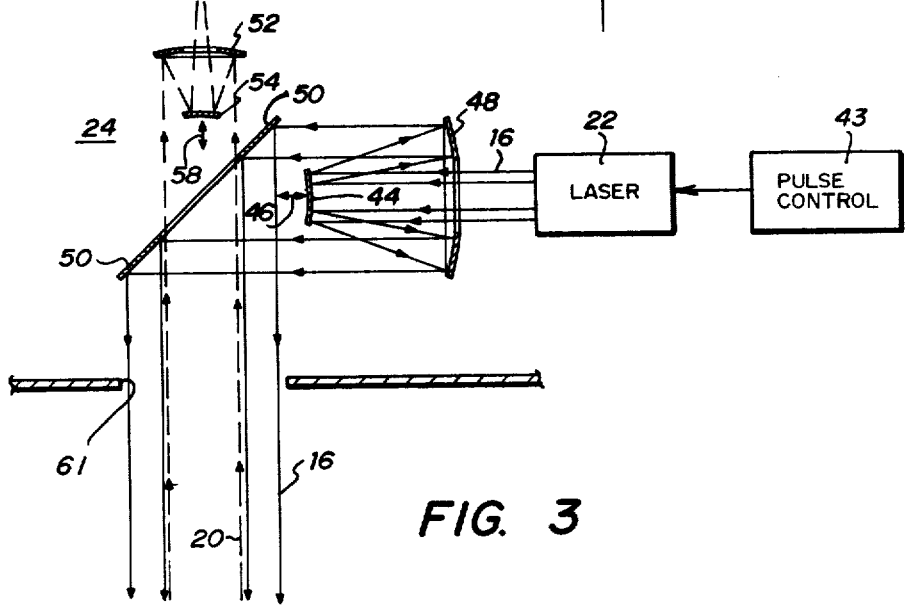
FIG. 3 is a schematic diagram of a laser focusing mechanism and spectrometer collection apparatus in accordance with the present invention.

The optical system 24 is schematically illustrated in greater detail in FIG. 3. The laser 22 is driven by a pulse control circuit 43 to generate the laser beam 16 which is annular and is directed to a focus mirror 44 moveable in the directions indicated by the arrow 46. An annular laser beam can be generated by using an unstable optical resonator. The mirror 44 reflects the annular laser beam 16 to a Cassegrain expander mirror 48 which in turn directs the beam to an annular flat reflector 50. The reflector 50 directs the laser beam as an annular converging beam toward the sample point 18 on the earth's surface. The focus mirror 44 is moved back and forth in the direction of the arrows 46 in order to focus the laser beam 16 to have a preselected diameter as it strikes the earth at the sample point 18. The radiation 20 generated by the vaporized mineral sample is returned to the optical system 24 to a converging reflector 52 which directs the radiation 20 to a focus reflector 54 which in turn directs the returned radiation into an entrance slit 56 of the spectrometer 28. The focus reflector 54 is moved in the direction of the arrows 58 in order to focus the image of the radiation 20 on the entrance slit 56.

The data produced by the spectrometer 28 is channeled to a recorder 60 which records the data to permit additional correlation and analysis after collection.

Both the downward directed laser beam 16 and the returned radiation 20 pass through a window 61 in the base of the aircraft 10. A suitable window material is zinc selenide, however, the window may alternatively be an opening in the aircraft.

The optical system illustrated in FIG. 3 generates a downward directed laser beam coaxial with the spectrometer line-of-sight to eliminate the problem of parallax which would be present if the coaxial orientation was not employed. The annular laser beam 16 generated by the laser 22 is a conventional coherent laser beam. The focus mirror 44 reflects this beam to the Cassegrain expander mirror 48. This mirror reflects the annular beam to the annular flat reflector 50. By movement of the focus mirror 44 in the direction of the arrows 46 the convergence of the beam is varied as it is provided to the annular flat reflector 50. The variation in this focus causes the beam 16, which is annular and conical, to be concentrated at a focus point. This focus point is selected to be of a predetermined size and the focus mirror 44 is adjusted to produce this focus point on the surface of the earth. The radiation 20 generated by the vaporized minerals is returned through the interior of the annular beam 16 and transferred to the optical elements 52 and 54 which direct the radiation into an entrance slit 56 of the spectrometer 28. The focus mirror 54 is positioned so as to project the image of the vaporized minerals from the sample point 18 into the spectrometer 28. Both the spectrometer optics and the laser optics are mounted on the same stabilized platform 30, and therefore, the spectrometer will at all times be aimed at the point of impact of the laser beam 16.

In operation over land areas the laser beam 16 as shown in FIG. 1 is directed at the sample point 18 on the surface of the earth with a power density sufficient to vaporize a sample of the surface material and then heat the resulting vapor to a temperature sufficient to yield atomic emission radiation, typically in the range from ultraviolet to near infrared. This radiation is returned to the spectrometer which measures the radiation wave lengths and intensities to determine the type of mineral vaporized. The analysis can reveal not only the types of minerals present but also the quantitative ratios of the minerals. A portion of the radiation 20 will be absorbed by various gases in the atmosphere but this absorption is well characterized and can easily be compensated for.

When a high-energy laser is operated in the atmosphere, a fraction of the energy of the laser is absorbed by the atmosphere thereby heating the air along the path of the laser beam. This heated air, which is of a differing density from surrounding air, creates an optical disturbance within the atmosphere to cause the laser beam to be diverged from its desired focus. In order to overcome this problem, the laser of the present invention is operated in a pulsed mode with the pulse width shorter than the thermalization time of the dominant radiation absorbing molecules (e.g., $CO_2$) of the air. Therefore, for each pulse, there is insufficient time for the air to be heated and create an optical disturbance to interfere with the beam. However, an optical disturbance is still created following the pulse, and if the next pulse is directed through the same air space, the optical distortion problem will again be encountered. But, since the aircraft is moving, the pulse-to-pulse interval is selected such that the aircraft advances by at least one beam aperture diameter between pulses. Hence, the line-of-sight from the aircraft to the surface spot is moved ahead of the disturbance created by the previous pulse.

Due to the short period and limited energy of the laser pulse, only a very thin layer of surface material will be vaporized by each of the pulses. The vapor produced by the pulse and caused to radiate will be representative of only the very thin layer which has been vaporized. Therefore, with a series of pulses directed to the same sample point deeper and deeper layers of material will be vaporized and therefore sampled. The power applied to the sample is of such magnitude that the surface material will virtually explode outward and clear the sample area for the next laser pulse. Therefore each sample will produce radiation substantially associated with only the particular layer which has been vaporized. This procedure is particularly useful in survey sampling of land areas where the rock structure is covered with a thin weathered layer which is chemically different from the bulk of the rock material. A typical type of weathered layer is referred to as "desert varnish" and is typically of a limited thickness which can be easily penetrated by the laser beam. At a sample point, the vapor produced by each laser pulse can be individually examined in real time and correlated with known spectra to provide instant identification of selected materials.

Since a number of laser pulses are directed to each sample point during a time period, the aircraft will move a given distance, therefore the aim of the laser beam must be compensated for this movement so that each of the pulses strikes the same sample point. The sample points themselves are selected at given distances along the track of the aircraft dependent upon the sample rate desired and the speed of the aircraft.

A set of operating parameters suitable for a wide-area mineral survey to be taken from a small aircraft are as follows. The laser is operated to generate pulses at a rate of 200 per second with each pulse having an energy level of 25 joules. Each pulse has a duration of 50 microseconds and a group of 20 pulses are directed to each sample point for each burst. The burst rate or rate of sampling is selected to be 1.333 per second. The output aperture diameter of the laser beam at the aircraft is 0.25 meters and the beam has a width of 17 arc secs.

These parameters are selected to be compatible with an aircraft speed of 85 meters/sec. (190 MPH) operating at an altitude of 100 meters (328 ft.) with a travel distance between bursts of 63.8 meters (209 ft.).

The diameter of the sample point is then 8 millimeters which together with the 25 joule energy level produces an energy density of 50 joules per square centimeter. In a typical rock sample this power level will produce a penetration for each pulse of 0.05 millimeters resulting in a total penetration with 20 pulses of 1.0 millimeter. This power level produces a surface irradiance of about 1 million watts per square centimeter with a peak electric field of about 25 kilovolts per centimeter. This electric field value is less than the dielectric strength of the air thereby preventing electrical breakdown of the air. The time periods of the pulses are so short as to lose only about 1% of the energy due to heat transfer to the surrounding rock.

A laser source suitable for use in the present invention is the model 971 gas transport laser manufactured by GTE Sylvania, modified for pulsed operation. This carbon dioxide laser produces a continuous output power of 5,000 watts with a 12 millimeter output beam. If the aircraft power system is inadequate to drive the laser, an outboard turbo alternator can be provided to generate the necessary electrical power. This laser operates at a wave length of 10.6 micrometers.

The spectrometer for use in the present system can be a model TN-1710 diode array rapid scan spectrometer system manufactured by Tracor Northern of Middleton, Wis. This system has a spectral response ranging from 200 to 1100 nanometers with a dynamic range of 4,096:1.

In a further embodiment of the present invention, a second lower power laser source 29 is employed to illuminate the zone of vaporization of the mineral sample after the high energy laser pulse has terminated. The atomic emission of the vaporized material decays rapidly due to expansion and cooling but the vapor itself remains present for a short period longer, and if this vapor is illuminated by a low power laser 29, for example, a nitrogen laser operating at 337.1 nanometers and emitting 5 millijoules of energy, remote Raman spectrometry of the vaporized material can be obtained before the vapor has diffused into the surrounding atmosphere. After the vapor itself has been diffused the same laser may be used to illuminate the freshly cleared surface and cause that surface to yield a fluorescence spectrum which can likewise be analyzed for mineral content. The second low power laser 29 can be pulsed after each high-energy laser pulse for analyzing each surface sample on a pulse for pulse basis. Thus, the atomic emission, Raman and fluorescence spectra can all be obtained in conjunction with each high-energy laser pulse for comprehensive analysis of the minerals at the sample point.

The analysis techniques described above are suitable for both day and night operation. For daytime surveying, concurrent photography can be used to advantage by synchronizing the camera shutter with the laser pulse. A flash of visible radiation will be produced from the irradiated spot which will be recorded along with the surrounding terrain to facilitate determination of the exact location of the sample point.

Although several embodiments of the invention have been illustrated in the accompanying drawings and described in the foregoing detailed description, it will be understood that the invention is not limited to the emobdiments disclosed but is capable of numerous rearrangements, modifications and substitutions without departing from the scope of the invention.

I claim:

1. A method for conducting a survey to determine the mineral content of the earth's surface in a selected region, comprising the steps of:
   (a) from an aircraft traversing said region, directing laser beam energy downward to a sample area on the surface with energy of such intensity that the laser beam energy causes surface material in said sample area to be vaporized thereby exposing underlying material such that the laser beam energy is directed to said underlying material with energy of such intensity to generate at least one of atomic emission radiation, Raman scattering radiation or fluorescence radiation characteristic of said underlying material,
   (b) collecting a portion of said radiation by optical apparatus carried by the aircraft, and
   (c) applying said collected radiation to a spectrometer for measuring the spectra characteristics of said radiation.

2. A method according to claim 1 where said underlying material is vaporized to generate atomic emission radiation.

3. A method according to claim 1 further including the step of directing pulsed laser beam energy to vaporize succeedingly deeper layers of said underlying material.

4. A method according to claim 1 further including the step of coaxially aligning said laser beam energy with the optical axis of said optical apparatus for reducing alignment errors due to parallax.

5. A method for conducting a survey to determine the mineral content of the earth's surface in a selected region comprising the steps of:
   (a) from an aircraft traversing said region, directing a first laser beam downward to impinge a sample of exposed surface material with such intensity to cause the exposed surface material to be vaporized,
   (b) directing said first laser beam to impinge a sample of subsurface material uncovered after vaporization of said exposed surface material, said first laser beam vaporizing a sample of said subsurface material,
   (c) directing a second laser beam downward to impinge the vaporized subsurface material,
   (d) collecting by optical apparatus carried by said aircraft scattered radiation produced when said second laser beam passes through said vaporized subsurface material, said scattered radiation characteristic of said vaporized subsurface material being due to the Ramam effect, and
   (e) applying said collected radiation to a spectrometer for measuring the spectra characteristics of said collected radiation.

6. A method according to claim 5 wherein said first and second laser beams are pulsed in an alternating repetitive sequence while being directed to said sample materials.

7. A method for conducting a survey to determine the mineral content of the earth's surface in a selected region comprising the steps of:
   (a) from an aircraft traversing said region, directing a first laser beam downward to impinge on a sample of exposed surface material with such intensity to cause the exposed surface material to be vaporized,
   (b) directing a second laser beam downward to said sample after said vaporized surface material has essentially dissipated, said second laser beam impinging upon newly exposed material for generating fluorescence radiation,
   (c) collecting by means of optical apparatus carried by said aircraft fluorescence radiation produced by said second laser beam and characteristic of said newly exposed material, and
   (d) applying said fluorescence radiation to a spectrometer for measuring the spectra characteristics of said fluorescence radiation.

8. A method according to claim 7 wherein said first and second laser beam are pulsed in an alternating repetitive sequence while being directed to said sample.

9. A method for conducting a survey to determine the mineral content of the earth's surface in a selected region, comprising the steps of:

(a) from an aircraft traversing said region, directing a sequence of laser beam pulses to a single sample area at the earth's surface, each said pulse impinging on the exposed surface material within said sample area with the power intensity of at least one of said pulses sufficient to cause exposed surface material to be converted into a vapor thereby exposing underlying mineral material, (b) directing said pulsed laser beam toward said exposed underlying mineral material after said surface material has been removed, said laser beam having a power intensity to cause said underlying material to be converted into a vapor, (c) collecting by means of optical apparatus carried by said aircraft portions of radiation from the underlying mineral material in said sample area generated by at least one of said laser beam pulses, and (d) applying said collected radiation to a spectrometer for measuring the spectra characteristics of said collected radiation.

10. Apparatus for conducting a mineral survey of the earth's surface in a selected region comprising in combination:

(a) an aircraft for traversing said region, (b) laser beam generation means transported by said aircraft for directing a laser beam to impinge a sample point on the earth's surface below said aircraft at an energy level to evacuate surface material from said sample point and expose underlying material to said laser beam, and (c) sensing means transported by said aircraft for receiving radiation characteristic of said underlying material at the sample point and for analyzing the radiation collected by said sensing means.

11. Apparatus according to claim 10 wherein said generation means comprises beam expander optics for receiving, enlarging and converging said beam to said sample point.

12. Apparatus according to claim 10 wherein said sensing means comprises a radiation collecting telescope and spectrometer.

13. Apparatus according to claim 10 wherein means are provided to direct said laser beam coaxially with the line of sight of said sensing means.

14. Apparatus for taking a mineral survey from an aircraft to determine the mineral constituents which make up the earth's surface in a selected region, in combination comprising:

(a) means transportable by said aircraft for generating a pulsed laser beam having sufficient power to vaporize and evacuate samples of the earth's weathered surface material thereby exposing underlying material and for directing said beam to a sample point in said underlying material, (b) a spectrometer transportable by said aircraft having optics for collecting radiation generated at said sample point, and (c) a stabilized platform supporting elements for assuring said laser beam is directed to said sample point and said spectrometer receives radiation from said sample point.

15. The system according to claim 14 wherein said laser beam is aligned coaxially with the line of sight of said spectrometer.

16. The system according to claim 14 including a second laser for generating a second laser beam and stabilized for directing said second laser beam towards said sample point on the earth's surface.

* * * * *